United States Patent
Yokota et al.

(10) Patent No.: US 9,659,366 B2
(45) Date of Patent: May 23, 2017

(54) IMAGE PROCESSING DISPLAY DEVICE AND AN IMAGE PROCESSING DISPLAY PROGRAM

(75) Inventors: Tetsuya Yokota, Nasushiobara (JP); Tomohiro Kawasaki, Otawara (JP); Satoshi Wakai, Nasushiobara (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 0 days.

(21) Appl. No.: 13/997,812

(22) PCT Filed: Aug. 10, 2012

(86) PCT No.: PCT/JP2012/070571
§ 371 (c)(1),
(2), (4) Date: Jun. 25, 2013

(87) PCT Pub. No.: WO2013/024831
PCT Pub. Date: Feb. 21, 2013

(65) Prior Publication Data
US 2013/0287282 A1  Oct. 31, 2013

(30) Foreign Application Priority Data
Aug. 18, 2011  (JP) ................................. 2011-178918

(51) Int. Cl.
*G06T 7/00* (2006.01)
*A61B 34/10* (2016.01)
(Continued)

(52) U.S. Cl.
CPC ............ *G06T 7/0012* (2013.01); *A61B 34/10* (2016.02); *A61B 6/12* (2013.01); *A61B 2034/102* (2016.02);
(Continued)

(58) Field of Classification Search
CPC ........ A61B 19/5244; A61B 2019/5251; A61B 2019/5272; A61B 2019/5458; A61B 2019/5483; A61B 6/12; G06T 3/0068
See application file for complete search history.

(56) References Cited

U.S. PATENT DOCUMENTS

| 6,532,380 B1 * | 3/2003 | Close ..................... A61B 6/481 382/128 |
| 8,073,221 B2 * | 12/2011 | Kukuk .................. G06T 7/0044 378/4 |

(Continued)

FOREIGN PATENT DOCUMENTS

| CN | 101856233 A | 10/2010 |
| JP | 2002-119502 A | 4/2002 |

(Continued)

OTHER PUBLICATIONS

International Search Report Issued Sep. 11, 2012 in PCT/JP12/070571 Filed Aug. 10, 2012.
(Continued)

*Primary Examiner* — Bhavesh Mehta
*Assistant Examiner* — Menatoallah Youssef
(74) *Attorney, Agent, or Firm* — Oblon, McClelland, Maier & Neustadt, L.L.P.

(57) ABSTRACT

An image processing display and an image processing display program that can prevent interference with catheter treatment even when the distal end of a catheter is located behind a treatment apparatus on X-ray fluoroscopic images. The image processing display displays X-ray fluoroscopic images to be obtained by looking through a region including blood vessels using X-rays during treatment, and includes a treatment apparatus image extractor and an image processor. The treatment apparatus image extractor, based on X-ray fluoroscopic images, extracts treatment apparatus images representing the treatment apparatus having the property of (Continued)

absorbing X-rays. The image processor determines the distal end position of the catheter to superimpose and display images representing the determined distal end position of the catheter on the region of the X-ray fluoroscopic images showing the treatment apparatus.

11 Claims, 11 Drawing Sheets

(51) Int. Cl.
    *A61B 6/12*     (2006.01)
    *A61B 90/00*     (2016.01)
    *A61B 34/20*     (2016.01)

(52) U.S. Cl.
    CPC . *A61B 2034/2065* (2016.02); *A61B 2090/376* (2016.02)

(56) References Cited

U.S. PATENT DOCUMENTS

| | | | |
|---|---|---|---|
| 2007/0032859 A1* | 2/2007 | Hornig | A61F 2/82 623/1.21 |
| 2007/0232898 A1 | 10/2007 | Huynh et al. | |
| 2008/0183071 A1* | 7/2008 | Strommer | A61B 5/06 600/424 |
| 2009/0281418 A1 | 11/2009 | Ruijters et al. | |
| 2010/0331950 A1* | 12/2010 | Strommer | A61B 5/0066 623/1.11 |

FOREIGN PATENT DOCUMENTS

| | | |
|---|---|---|
| JP | 2004 501723 | 1/2004 |
| JP | 2006 194502 | 7/2006 |
| JP | 2007-500565 A | 1/2007 |
| JP | 2008 178686 | 8/2008 |
| JP | 2009-532127 A | 9/2009 |
| JP | 2009 532162 | 9/2009 |
| JP | 2010 240253 | 10/2010 |
| JP | 2011 139821 | 7/2011 |
| WO | 2005 011499 | 2/2005 |

OTHER PUBLICATIONS

Combined Chinese Office Action and Search Report issued Dec. 15, 2014 in Patent Application No. 201280009612.6 (with English Translation of Category of Cited Documents).

Office Action issued Apr. 7, 2015 in Japanese Patent Application No. 2011-178918.

Office Action mailed Dec. 1, 2015 in Japanese Patent Application No. 2011-178918.

* cited by examiner

IMAGE PROCESSING DISPLAY DEVICE AND AN IMAGE PROCESSING DISPLAY PROGRAM

TECHNICAL FIELD

The embodiments of the present invention relate to an image processing display device and an image processing display program.

BACKGROUND ART

Recently, a new system known as hybrid treatment has been developed. For example, this treatment is performed by combining bypass surgery and catheter treatment in such a manner that the bypass surgery is carried out on coronary arteries in a short time for which the catheter treatment is difficult while simultaneously carrying out the catheter treatment on the remaining coronary lesions. By taking advantage of both treatments, the hybrid treatment allows complete revascularization to be performed more safely.

In bypass surgery, a treatment apparatus such as a stent graft or an embolization coil is inserted into arteries. Some treatment apparatuses have the property of absorbing X-rays. In the catheter treatment, X-ray fluoroscopic images are used.

A technique is known in the art, wherein information registered in a database is read out from the distal end position of a surgical tool detected by a position detector as well as the pixel position of the volume data corresponding to the distal end position of the surgical tool and the necessary information is provided to an operator (Patent Document 1).

PRIOR ART DOCUMENT

Patent Document

[Patent Document 1] Japanese Unexamined Patent Application Publication No. 2006-194502

SUMMARY OF THE INVENTION

Problems to be Solved by the Invention

However, when performing the catheter treatment, there was a problem such that, for example, the treatment apparatus inserted during bypass surgery appears in the X-ray fluoroscopic images, and the distal end position of the catheter located behind the treatment apparatus is not displayed, therefore interfering with catheter treatment.

The embodiments are intended to solve the above-mentioned problem, and the its object is to provide an image processing display device and an image processing display program that can prevent interference with the catheter treatment even when the distal end of the catheter is located behind the treatment apparatus on the X-ray fluoroscopic images.

Means of Solving the Problems

In order to solve the above-mentioned problem, the image processing display device according to the embodiments displays X-ray fluoroscopic images to be derived by X-ray fluoroscopic imaging of a region including blood vessels during treatment, and comprises a treatment apparatus image extractor and an image processor. The treatment apparatus image extractor, based on X-ray fluoroscopic images, extracts treatment apparatus images representing a treatment apparatus with the property to absorb X-rays. The image processor determines the distal end position of the catheter to superimpose and display images representing the determined position in the region appearing on the X-ray fluoroscopic images.

MODES FOR CARRYING OUT THE INVENTION

[The First Embodiment]

The first embodiment of the image processing display device is described with reference to respective figures. Here, an image processing display device is described in a case applied for hybrid treatment such that small incision coronary artery bypass surgery and catheter treatment are simultaneously performed.

Figure 1:
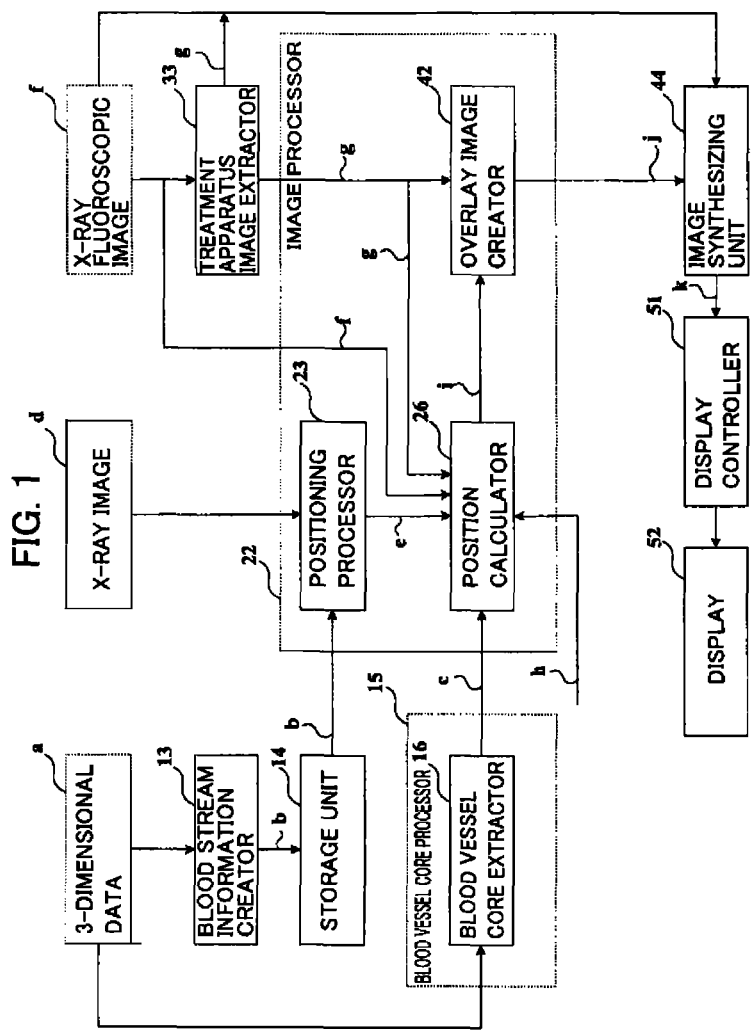
FIG. 1 is a functional block diagram of an image processing display device according to the first embodiment.
Figure 2:
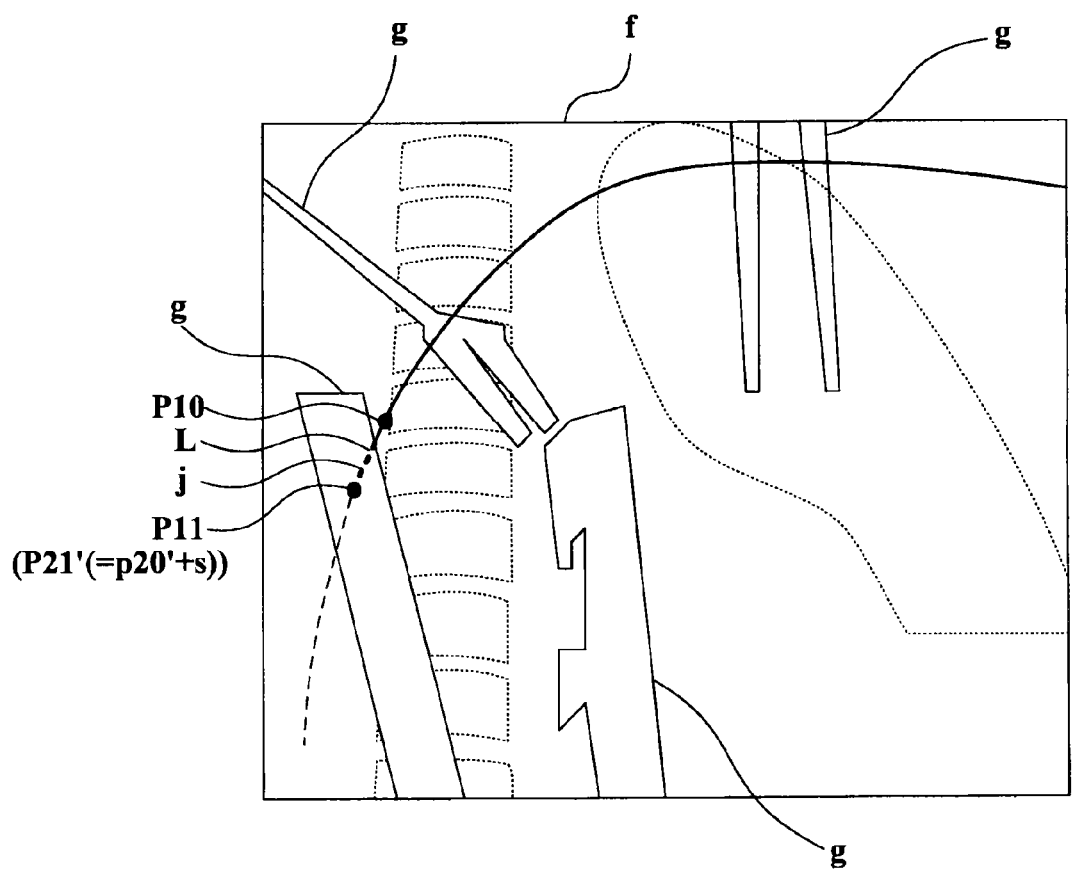
FIG. 2 is a view showing an example in which 2-dimensional images of the distal end of a catheter are superimposed and displayed on X-ray fluoroscopic images.

FIG. 1 is a functional block diagram of the image processing display device, while FIG. 2 is a view showing an example in which 2-dimensional images of the distal end of a catheter are superimposed and displayed on X-ray fluoroscopic images.

As shown in FIG. 1, the image processing display device comprises a blood stream information creator 13, a storage unit 14, a blood vessel core processor 15, an image processor 22, a treatment apparatus image extractor 33, an image synthesizing unit 44, a display controller 51, and a display 52.

In the preliminarily stage or the initial stage of the hybrid treatment, 3-dimensional data in a region including blood vessels (indicated by a in FIG. 1) and 2-dimensional X-ray images of the blood vessels (indicated by d in FIG. 1) are obtained.

The 3-dimensional data (the volume data) in the region including the blood vessels is obtained from a medical diagnosis device (for example, an X-ray CT device). The 3-dimensional data can be read out from a storage device on the Internet (including the storage device of the medical diagnosis device). Further, the 3-dimensional data may be stored in the storage device of the image processing display device.

X-ray images of the blood vessels are obtained by an X-ray angiographic examination. According to this examination using the medical diagnosis device (for example, X-ray equipment), by exposing X-rays after pouring a contrast agent into the target blood vessels that does not easily permit the passage of X-rays, the form of the blood vessels containing the contrast agent is highlighted. The X-ray images of the blood vessels obtained by the examination can be read out from the storage device of the medical diagnosis device (including a buffer). Further, the X-ray images of the blood vessels may be stored in the storage device on the Internet or in the storage device of the image processing display device, and the X-ray images may be capable of being read from these storage devices.

For example, in the orthogonal coordinates with the x1-axis, y1-axis, and z1-axis being orthogonal to each other, when the X-ray exposure direction of the blood vessels is in the z1 axial direction, the plane pixel coordinates of an X-ray image d of the blood vessels are (x1, y1). When storing the X-ray image d of the blood vessels in the storage device, the plane pixel coordinates of the X-ray image d of the blood vessels and the plane coordinates of a memory address are preliminarily related with each other.

(Storage Unit)

The blood stream information creator 13 extracts a 3-dimensional image b representing blood vessels based on 3-dimensional data a. The extracted 3-dimensional image b of the blood vessels is stored in the storage unit 14.

For example, when defining the x2 axial direction as the alignment direction of an X-ray detection element (not shown), the y2 axial direction as the body axial direction (sliced direction), and the z2 axial direction as the direction that is orthogonal to the x2-axis and y2-axis, the spatial coordinates are (x2, y2, z2). When storing the 3-dimensional image b of the blood vessels in the storage unit 14, the space voxel coordinates of the blood vessels 3-dimensional image b and the spatial coordinates of the memory address are preliminarily related with each other.

(Blood Vessel Core Processor)

The blood vessel core processor 15 comprises a blood vessel core extractor 16 for extracting a 3-dimensional blood vessel core image (c shown in FIG. 1) representing blood vessel cores. Various methods of extracting the 3-dimensional image b of the blood vessels and the blood vessel core image c have been suggested, however, in the present embodiment, any publicly known methods may be employed. Further, the 3-dimensional image b of the blood vessels may be referred to as blood stream information. In addition, in some cases, the blood vessel core image c is described included in the blood stream information.

In the hybrid treatment, a medical diagnosis device (for example, an X-ray system for diagnosis) performs X-ray fluoroscopic imaging on a region including the blood vessels to obtain X-ray fluoroscopic data, and then a X-ray fluoroscopic images (indicated by f in FIG. 1) is created based on the X-ray fluoroscopic data. Further, the X-ray fluoroscopic image f may be stored in the storage device of the image processing display device. Here, the X-ray photographing direction for creating the X-ray fluoroscopic image f and the X-ray photographing direction for obtaining the X-ray image d of the blood vessels in the X-ray angiographic examination are set equally.

[Image Processor]

The image processor 22 includes a positioning processor 23, a position calculator 26, and an overlay image creator 42.

(Positioning Processor)

The positioning processor 23 obtains a corresponding positional relation of the 3-dimensional image b of the blood vessels with the X-ray image d of the 2-dimensional blood vessels by aligning the 3-dimensional image b of the blood vessels on the X-ray image d of the 2-dimensional blood vessels. The reason for this is that, using the X-ray image d of the blood vessels alone, it is not possible to determine the positions of two objects which one is in front of the other, when the objects are displayed to be superimposed each other, on the X-ray fluoroscopic image f.

The 3-dimensional image b of the blood vessels is aligned on the X-ray image d of the blood vessels by converting (reversing, enlarging, reducing, moving in parallel) the coordinates (x2, y2, z2) of the 3-dimensional image b of the blood vessels. The coordinates (x2, y2, z2) of the 3-dimensional image b of the blood vessels are converted by means of a 3-dimensional coordinates convertor (not shown).

For example, first, by rotating the coordinates (x2, y2, z2) of the 3-dimensional image b of the blood vessels, the x2-axis and the y2-axis are aligned with the x1-axis and the y1-axis of the plane coordinates (x1, y1) of the blood vessels. The aligned axes are defined as x2', y2', and z2', respectively. Next, in the plane coordinates (x1, y1), and (x2, y2), the coordinates (x2', y2', z2') of the 3-dimensional image b of the blood vessels are enlarged and reducted such that the distances between 2 predetermined points are equal. Further, depending on the case, the coordinates of the 3-dimensional image of the blood vessels are moved in parallel.

In the following description, the coordinates of the 3-dimensional image b of the blood vessels after being aligned at the coordinates (x1, y1) of the X-ray image d of the blood vessels are defined as (x2', y2', z2').

In the conversion of coordinates by the 3-dimensional coordinates convertor, when the coordinates of a memory address space are defined as (x2, y2, z2) and the converted coordinates as (x2', y2', z2'), conversion of the coordinates such as by rotation, reversion, enlargement, reduction, and parallel movement can be performed by controlling the values of a coefficient matrix vector A and a vector B for parallel movement via affine transformation.

The affine transformation is represented by the following formula.

$$\begin{bmatrix} x2' \\ y2' \\ z2' \end{bmatrix} = A \begin{bmatrix} x2 \\ y2 \\ z2 \end{bmatrix} + B$$

where A and B are represented as follows:

$$A = \begin{bmatrix} a & b & c \\ d & e & f \\ g & h & i \end{bmatrix}$$

-continued $$B = \begin{bmatrix} x0 \\ y0 \\ z0 \end{bmatrix}$$

For example, the vector A to be rotated from the z-axis in a positive direction at an angle θ around the y-axis is represented by the following formula.

$$A = \begin{bmatrix} \cos\theta & -\sin\theta & 0 \\ \sin\theta & \cos\theta & 0 \\ 0 & 0 & 1 \end{bmatrix}$$

In this case, if there is no parallel movement, the vector B is represented by the following formula.

$$B = \begin{bmatrix} 0 \\ 0 \\ 0 \end{bmatrix}$$

As described above, by controlling the values of the vectors A and B and rotating, reversing, enlarging, reducting, and moving in parallel the coordinates (x2, y2, z2) of the 3-dimensional image of the blood vessels, it is possible to adjust the position of the 3-dimensional image b with respect to the X-ray image d of the blood vessels. Thereby, it is possible to obtain the corresponding positional relation of the 3-dimensional image of the blood vessels to the X-ray image of the blood vessels. The positioning information (vectors A, B) is indicated by e in FIG. 1.

In addition, based on the positioning information e, it is possible to relate any position on the coordinates of the 3-dimensional image b of the blood vessels to any position of the coordinates of the X-ray image d of the blood vessels.

The treatment apparatus image extractor 33 extracts the treatment apparatus images (indicated by g in FIG. 1) representing the treatment apparatus inserted during bypass surgery, based on the X-ray fluoroscopic image f. With respect to extraction of the treatment apparatus images g, various methods have been suggested; however, the present embodiment may adopt any publicly known methods. The treatment apparatus image g is extracted as an image of the outline of the treatment apparatus (refer to FIG. 2).

(Position Calculator)

The position calculator 26 obtains the distal end position of the catheter as well as the traveling direction of the catheter. In order to obtain the position, and the like of the distal end of the catheter, there are a case such that the X-ray fluoroscopic image f is used, and a case such that the blood vessel core image c, the positioning information e, the treatment apparatus images g, and operational information (indicated by h in FIG. 1) according to the catheter are used. Here, the operational information according to the catheter is the movement amount of the catheter made by the operation of an operator. For example, a sensor for detecting the movement amount of the catheter is provided at the position where the catheter is inserted into the test object. A value determined based on the result of the above detection is the operational information according to the catheter, and hereinafter, it is simply referred to as "the operational information." The position calculator 26 is one example of "a unit configured to determine the distal end position of the catheter."

First, it is described that the X-ray fluoroscopic image f is used when determining the position, and the like of the distal end of the catheter.

By reading out two X-ray fluoroscopic images f taken at specific intervals and calculating the difference between these two images, the position calculator 26 determines the position as well as the travelling direction of the distal end of the catheter based on the movement of the catheter shadow included in these images f.

As described above, when the catheter shadows are respectively included in two X-ray fluoroscopic images f, and the shadows are moved, the position calculator 26 is able to determine the position, and the like of the distal end of the catheter by using these images f.

On the contrary, even if the catheter shadows are respectively included in two X-ray fluoroscopic images f, when the movement of the catheter shadows is not exposed due to the distal end of the catheter being hidden behind the treatment apparatus, the position calculator 26 is not able to determine the position, and the like of the distal end of the catheter even using these images f.

In other words, when it is determined that the catheter shadow is not superimposed on the treatment apparatus images g as the outline image of the treatment apparatus, the position calculator 26 uses the X-ray fluoroscopic images f to determine the position, and the like of the distal end of the catheter. On the other hand, when it is determined that the catheter shadow is superimposed on the treatment apparatus images g, the position calculator 26 uses not the X-ray fluoroscopic images f but the blood vessel core images c, and the like.

In addition, in the internal memory of the position calculator 26, a position p10 (shown in FIG. 2) of the distal end of the catheter before the catheter shadow is superimposed on the treatment apparatus image g is stored along with the operational information h representing moving amount s of the catheter from the position p10. The position p10 is indicated as a point with the coordinates (x1, y1) of the X-ray image d of the blood vessels. Further, the moving amount s is indicated as the moving amount along the blood vessel cores with the coordinates (x2', y2', z2') of the 3-dimensional image b of the blood vessels.

Next, a case in which the blood vessel core images c, and the like are used instead of using the X-ray fluoroscopic image f when determining the distal end position of the catheter, and the like will be described.

The position calculator 26 relates the position p10 of the distal end of the catheter stored in the internal memory to a position p20' on the coordinates of the 3-dimensional image b of the blood vessels based on the positioning information e. Further, using the operational information h, the position calculator 26 calculates a position p21' of the distal end of the catheter that is moved from the position p20' along the blood vessel cores by the moving amount s (p21'=(p20'+s)). Further still, the position calculator 26 determines a position p11 (shown in FIG. 2) on the coordinates of the X-ray image d of the blood vessels related to the position p21'. The image of a line segment L from the position p10 to the position p11 is sent to the overlay image creator 42 as position information (indicated by i in FIG. 1) of the distal end of the catheter.

(Overlay Image Creator)

The overlay image creator 42 creates an image in which the image of the line segment L (shown in FIG. 2) is superimposed on the treatment apparatus image g based on the position information i and the treatment apparatus image g. This superimposed image is 2-dimensional image (indicated by j in FIG. 1) of the distal end of the catheter. The 2-dimensional image j of the distal end of the catheter is indicated by a broken line in FIG. 2.

(Image Synthesizing Unit, Display Controller)

The image synthesizing unit 44 synthesizes the X-ray fluoroscopic image f and the 2-dimensional image j of the distal end of the catheter to output synthesized image k to the display controller 51. The display controller 51 allows the display 52 to display the synthesized image k.

Thereby, it is possible to prevent interference with the catheter treatment as the 2-dimensional image j of the distal end of the catheter is superimposed and displayed on the X-ray fluoroscopic image f even when the distal end of the catheter is hidden behind the treatment apparatus.

Figure 3:
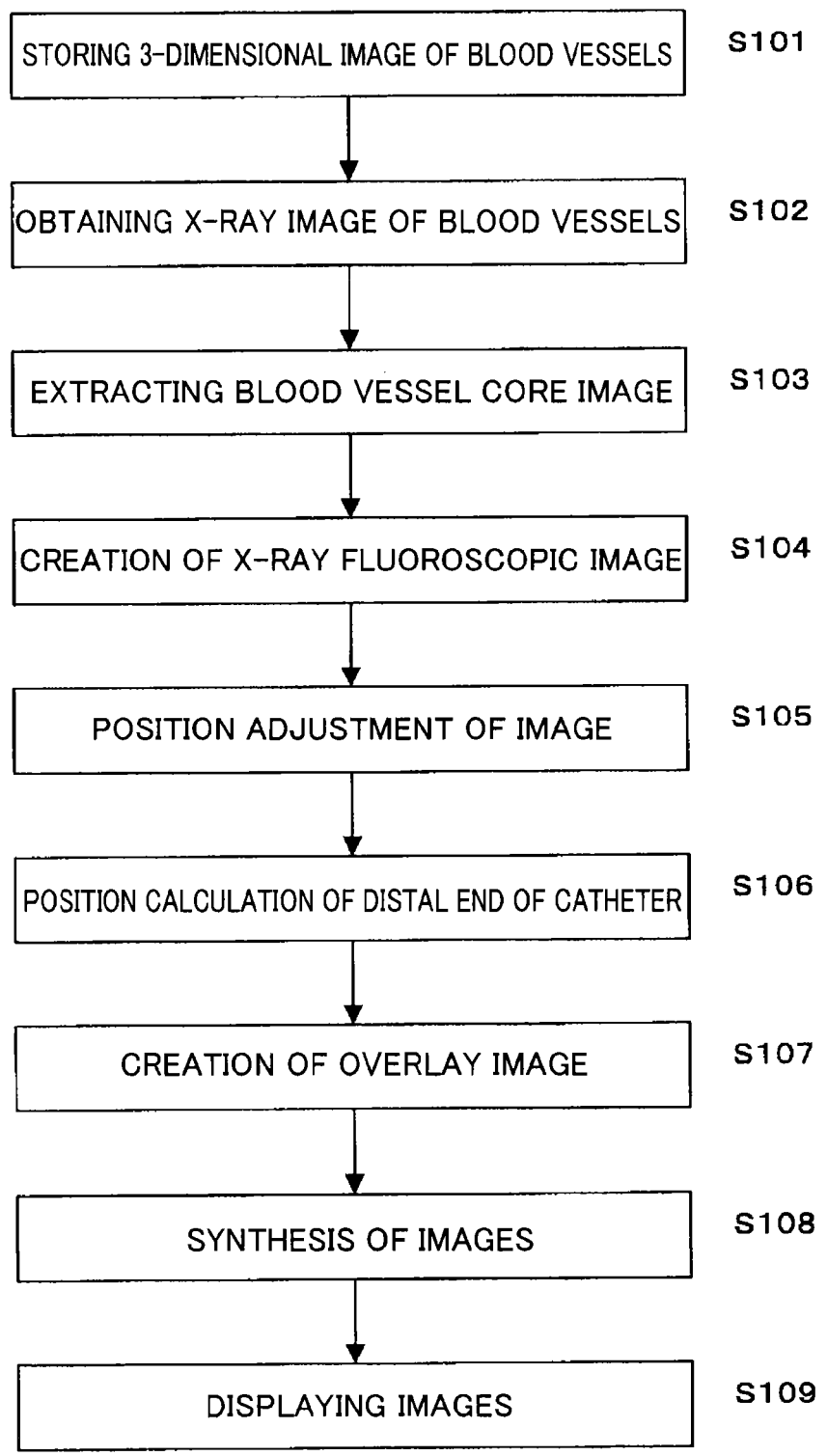
FIG. 3 is a flow chart showing a sequence of processes for image processing display during hybrid treatment.

Next, a sequence of processes for image processing display will be described with reference to FIG. 3. FIG. 3 is a flow chart showing the sequence of processes for image processing display during hybrid treatment.

(Step 101: Preliminarily Stage)

As shown in FIG. 3, in the preliminarily stage or the initial stage of the hybrid treatment, the 3-dimensional image b of the blood vessels is stored in the storage unit 14 in advance.

(Step 102: Preliminarily Stage)

Further, in the preliminarily stage or the initial stage of the hybrid treatment, the X-ray image d of the blood vessels is obtained in advance.

(Step 103: Blood Vessel Core Processing)

The blood vessel core extractor 16 extracts the 3-dimensional blood vessel core image c representing the blood vessel core, based on the 3-dimensional data a of the blood vessels.

(Step 104: Creation of X-Ray Fluoroscopic Image)

The X-ray fluoroscopic image f is created based on the X-ray fluoroscopic data. The X-ray photographing directions for both creating X-ray fluoroscopic image f and obtaining the X-ray image d of the blood vessels are set equally. Further, based on the X-ray fluoroscopic image f, the treatment apparatus image g representing the treatment apparatus is extracted.

(Step 105: Positioning Processing)

The positioning processor 23 adjusts the position of the 3-dimensional image b of the blood vessels with respect to the X-ray image d of the blood vessels. Thereby, the positioning information e is determined.

(Step 106: Calculation of Position)

The position calculator 26 determines the position as well as the travelling direction of the distal end of the catheter based on the blood vessel core image c, the operational information h, the positioning information e, the X-ray fluoroscopic image f, and the treatment apparatus image g.

When there is a difference in the X-ray fluoroscopic images f, the position calculator 26 determines the position as well as the travelling direction of the distal end of the catheter based on each of the X-ray fluoroscopic images f. When there is no difference in the X-ray fluoroscopic images f, the position calculator 26 determines the position as well as the travelling direction of the distal end of the catheter, based on the blood vessel core image c, the operational information h, the positioning information e, and the treatment apparatus image g.

(Step 107: Creation of Overlay Image)

The overlay image creator 42 creates images in which the image of the line segment L is superimposed on the treatment apparatus image g, based on the position information i and treatment apparatus image g.

(Step 108: Synthesis of Images)

The image synthesizing unit 44 synthesizes the X-ray fluoroscopic image f and the 2-dimensional image j of the distal end of the catheter.

(Step 109: Display)

The display controller 51 superimposes and displays the 2-dimensional image j of the distal end of the catheter on the X-ray fluoroscopic image f.

According to the first embodiment, in the positioning processing of step 105, the relative positional relation (the positioning information e) of the 3-dimensional image b of the blood vessels with respect to the X-ray image d of the blood vessels is determined. This serves to determine highly accurate positioning information e by comparing information on the blood vessels with each other; however, if high accuracy is not expected, the positioning information of the 3-dimensional image b of the blood vessels with respect to the X-ray fluoroscopic image f may be determined.

According to the first embodiment, using the blood vessel core image c and the operational information h according to the catheter, the distal end of the catheter is determined. Therefore, for example, a unit such as for generating signals from the distal end of the catheter and determining the distal end position of the catheter based on the generated signals is not required, and it is possible to perform the catheter treatment without using the apparatus provided with such the above unit, enhancing the general versatility and prevent growth in size of the apparatus.

[The Second Embodiment]

Next, the second embodiment of the image processing display device is described with reference to FIGS. 4 to 7.

In the second embodiment, with respect to the elements having the same configurations as those of the first embodiment, the same numbers are provided and the explanation thereof is omitted.

In the first embodiment, the distal end of the catheter is located behind the treatment apparatus in the photographing direction of the X-rays, making it impossible to take photographs of the distal end of the catheter. Therefore, the position calculator 26, using the operational information h, outputs the position information i of the distal end of the catheter to the overlay image creator 42, and the overlay image creator 42 is capable of creating the image j of the distal end of the catheter.

Figure 4:
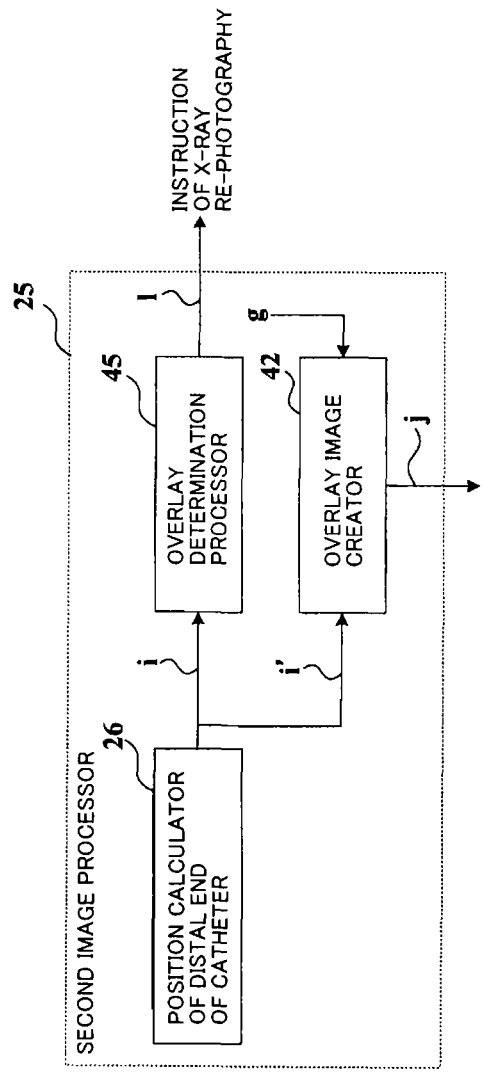
FIG. 4 is a functional block diagram of an image processor according to the second embodiment.

FIG. 4 is a functional block diagram of an image processor according to the second embodiment. As shown in FIG. 4, an overlay determination processor 45 is added to the image processor 25.

Receiving the position information i from the position calculator 26, the overlay processor 45 outputs X-ray re-photography instructions (indicated by 1 in FIG. 4) to the X-ray equipment.

According to the second embodiment, by changing the angle in the projection direction of the X-rays, direct exposure of the distal end of the catheter, by the X-rays without interference (X-ray re-photography). Using newly obtained X-ray fluoroscopic images through this X-ray re-photography, the distal end position of the catheter is determined.

A method of determining an angle in the projection direction of the X-rays of the X-ray re-photography is described with reference to FIGS. 5 to 7.

Figure 5:
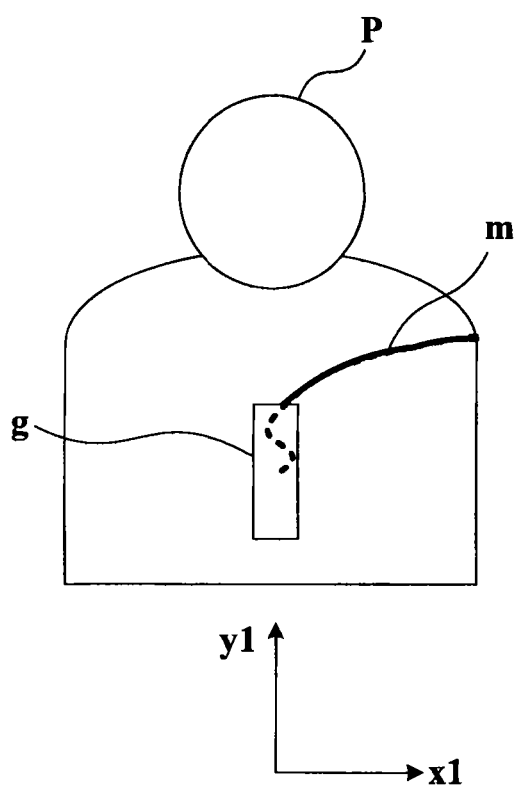
FIG. 5 is an exemplary diagram showing a test object, a treatment apparatus image, and a catheter shadow.

FIG. 5 is an exemplary diagram showing a test object P, a treatment apparatus image g, and a catheter shadow m. FIG. 6 is an exemplary diagram showing the test object P, an X-ray source 1, and an X-ray detector 2, and the like which are used for exposing X-rays at an angle $\theta=0$ in the X-ray photographing direction. FIG. 7 is an exemplary diagram showing the test object P, the X-ray source 1, and the X-ray detector 2, and the like which are used for exposing X-rays at an angle θ=θ1 in the X-ray photographing direction. Here, the angle θ in the X-ray photographing direction means the angle of rotation from the z1-axis in a positive direction around the y1-axis.

When the position calculator 26 determines that the catheter shadow (indicated by m in FIG. 5) is superimposed on the treatment apparatus images g as the image representing the outline of the treatment apparatus, the position calculator 26 outputs the X-ray re-photography instructions to the X-ray equipment (the medical diagnosis device). The X-ray re-photography instructions include the information of the angle θ1 in the projection direction of the X-rays to be used for the X-ray re-photography.

The position calculator 26 determines the angle θ1 in the projection direction of the X-rays upon X-ray re-photography.

Figure 6:
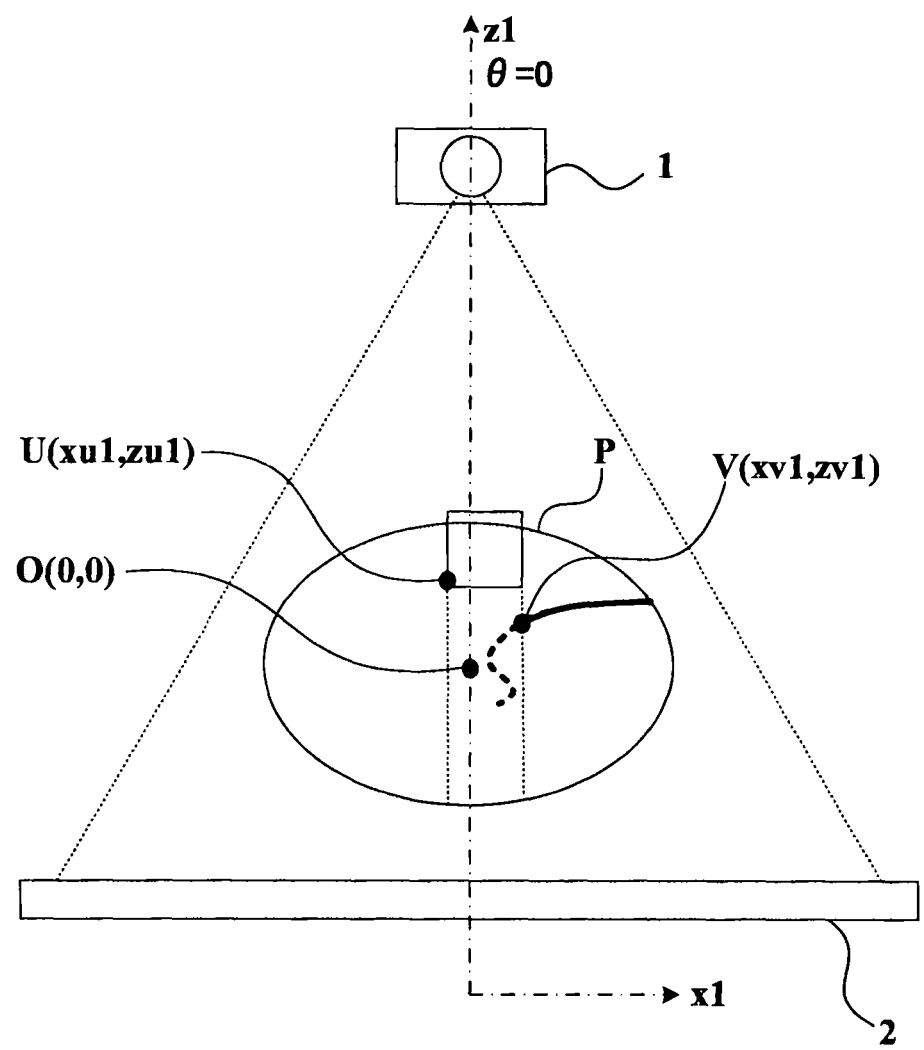
FIG. 6 is an exemplary diagram showing a test object, an X-ray source, an X-ray detector, and the like which are used for X-rays exposure at an angle $\theta=0$ in the X-ray photographing direction.

FIG. 6 illustrates a position U of the treatment apparatus on the coordinates (x1, z1) as (xu1, zu1) and a position V on the coordinates (x1, z1), where the catheter shadow m is superimposed on the treatment apparatus image g representing the outline of the treatment apparatus, as (xv1, zv1).

Figure 7:
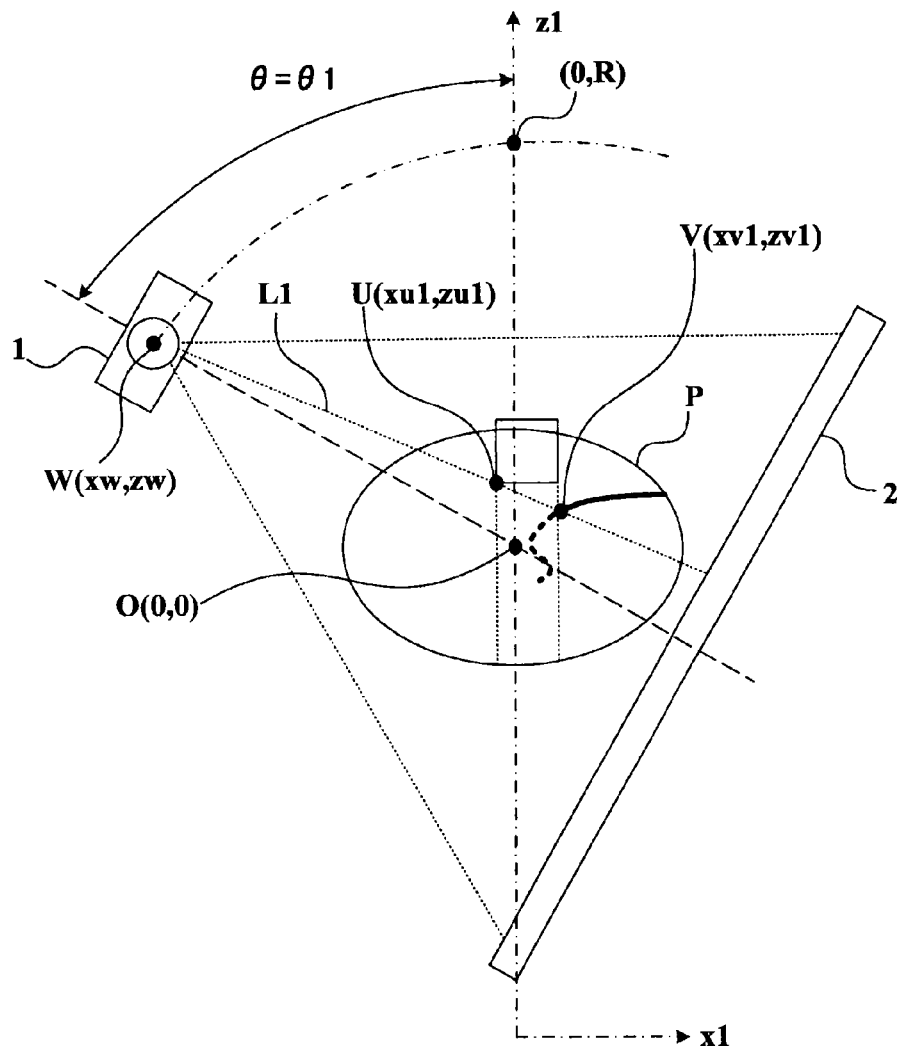
FIG. 7 is an exemplary diagram showing a test object, an X-ray source, an X-ray detector, and the like which are used for X-rays exposure at an angle $\theta=\theta_1$ in the X-ray photographing direction.

FIG. 7 illustrates an X-ray source 1 to be rotated with a radius R around the y1-axis as a center O (0, 0) on the coordinates (x1, z1).

As described above, the rotational trajectory of the X-ray source 1 is represented by the following formula.

$$x1^2 + z1^2 = R$$

An intersection point W connecting a circle represented by the above formula and a straight line L1 connecting two positions U (xu1, zu1) and V (xv1, zv1) is determined as (xw, zw).

An angle θ1 made by a straight line connecting the intersection point W (xw, zw) to the center O (0, 0) and the z1-axis is determined.

By changing the angle θ in the projection direction of the X-rays from 0 to θ1 and performing X-ray re-photography, an X-ray fluoroscopic image f' is newly obtained.

Figure 8:
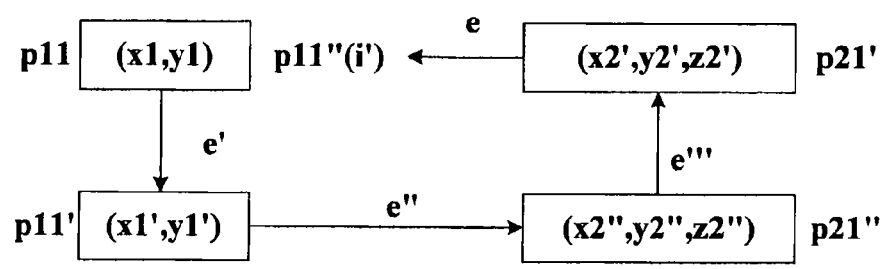
FIG. 8 is a view showing an example of an order for determining the distal end position of the catheter based on newly obtained X-ray fluoroscopic images taken at the angle $\theta_1$ in the X-ray photographing direction.

Next, based on the angle θ1 in the X-ray photographing direction and the newly obtained X-ray fluoroscopic image, an example of an order for determining the distal end position of the catheter is described with reference to FIG. 8. FIG. 8 is a view showing the order for determining the distal end position of the catheter.

As described in the first embodiment, it is considered that the coordinates (x1, y1) of the X-ray image d of the blood vessels and the coordinates (x2', y2', z2') of the 3-dimensional image b of the blood vessels are aligned. In this case, the positioning information is e.

In FIG. 8, the coordinates converted from the coordinates (x1, y1) of an X-ray image d' of the blood vessels are represented as (x1', y1'), and the coordinates of the 3-dimensional image b' of the blood vessels aligned to the coordinates (x1', y1') are represented as (x2", y2", z2").

Further, the conversion information from the coordinates (x1, y1) to the coordinates (x1', y1') is defined as positioning information e', the positioning information when the coordinates (x1', y1') and the coordinates (x2", y2", z2") are aligned is defined as positioning information e", and the conversion information from the coordinates (x2", y2", z2") to the coordinates (x2', y2', z2') is defined as positioning information e'".

The position calculator 26, based on the X-ray fluoroscopic image f' and the positioning information e', determines position p11' with the coordinates (x1', y1') corresponding to the position P11 with the coordinates (x1, y1). Further, the position calculator 26, based on the positioning information e", determines position p21" with the coordinates (x2", y2", z2") corresponding to the position p11'. Furthermore, the position calculator 26 determines position p21' with the coordinates (x2', y2', z2') corresponding to the position P21". Further still, the position calculator 26, based on the positioning information e, determines position p11" with the coordinates (x1, y1) of the X-ray image d of the blood vessels related to the position p21'. Here, the positions P11, P11', P11", P21', and P21" indicate the positions of the distal end of the catheter with the respective coordinates.

The position p11" at (x1, y1) is sent to the overlay image creator 42 as the position information i' of the distal end of the catheter. The overlay image creator 42, based on the position information i' and the treatment apparatus image g, creates the 2-dimensional image j of the distal end of the catheter.

According to the above-mentioned second embodiment, it is possible to determine the position information i' of the distal end of the catheter without using the operational information h according to the catheter.

[The Third Embodiment]

Figure 9:
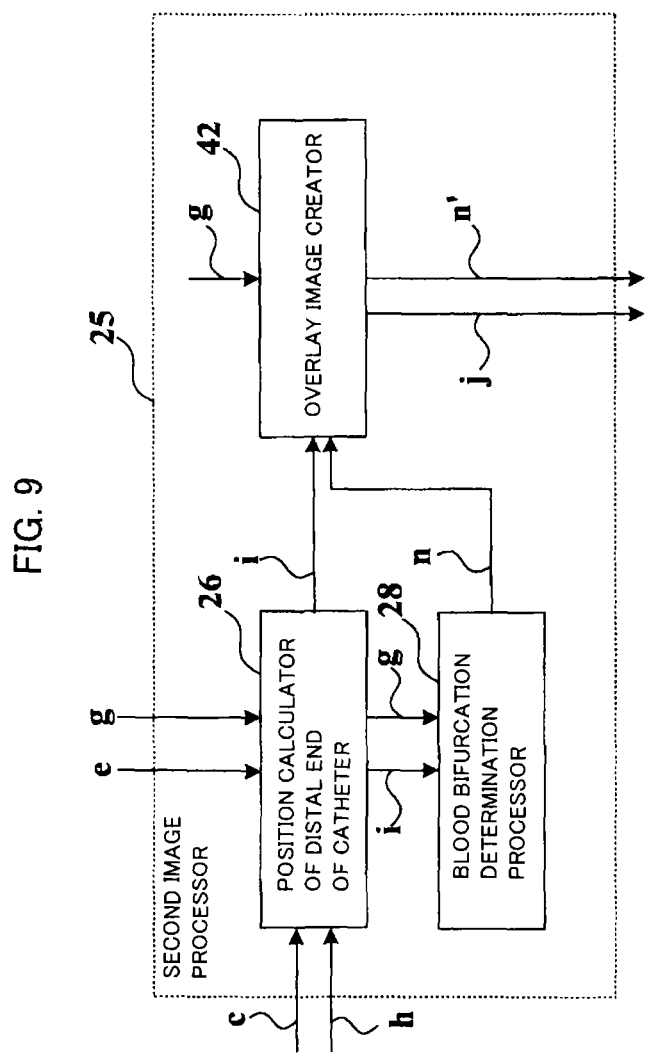
FIG. 9 is a functional block diagram of an image processor according to the third embodiment.

Next, with reference to FIG. 9, the third embodiment of the image processing display device is described.

In the third embodiment, with respect to the elements having the same configurations as those of the first embodiment, the same numbers are provided and the explanation thereof is omitted.

FIG. 9 is a functional block diagram of an image processor. As shown in FIG. 9, a blood bifurcation determination processor 28 is added to the image processor 25.

The blood bifurcation determination processor 28 creates 2-dimensional images (indicated by n in FIG. 9) of the blood bifurcations related to the X-ray fluoroscopic images upon receiving the position information i from the position calculator 26.

The method of creating the 2-dimensional image n of the blood bifurcations is basically the same as that of calculating the position information i of the distal end of the catheter by the position calculator 26 in the first embodiment.

According to the first embodiment, the position calculator 26 determines the position information i of the distal end of the catheter using the X-ray fluoroscopic image f, the blood vessel core image c, the positioning information e, the treatment apparatus image g, and the operational information h according to the catheter. According to the third embodiment, however, the position calculator 26 determines the 2-dimensional image n of the blood bifurcations using the X-ray fluoroscopic image f, the blood vessel core image c, the positioning information e, and the treatment apparatus image g.

The overlay image creator 42, based on the treatment apparatus image g and the 2-dimensional image n of the blood bifurcations, creates a superimposed image n' of the blood bifurcations in which the 2-dimensional image n of the blood bifurcations is superimposed on the treatment apparatus image g.

According to the third embodiment, not only the 2-dimensional image j of the distal end of the catheter but also the superimposed image n' of the blood bifurcations are displayed on the X-ray fluoroscopic image f, making it possible to perform the operation of the catheter without any problem.

[The Fourth Embodiment]

Figure 10:
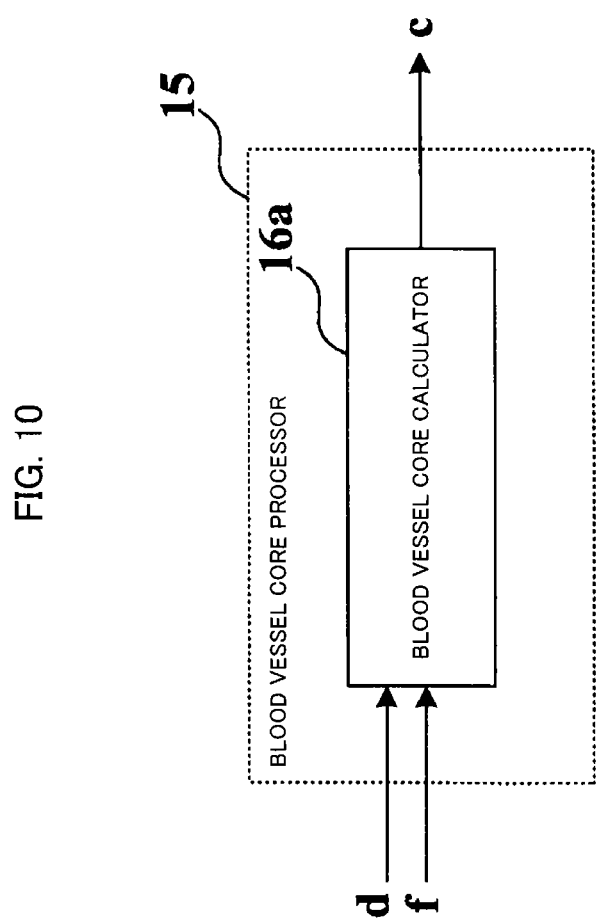
FIG. 10 is a functional block diagram of a blood vessel core processor according to the fourth embodiment.

Next, with reference to FIG. 10, the fourth embodiment of the image processing display device is described.

In the fourth embodiment, with respect to the elements having the same configurations as those of the first embodiment, the same numbers are provided and the explanation thereof is omitted.

FIG. 10 is a functional block diagram of a blood vessel core processor. As shown in FIG. 10, a blood vessel core calculator 16a is provided with the blood vessel core processor 15 in place of the blood vessel core extractor 16.

According to the first embodiment, the blood vessel core processor 15 is provided with the blood vessel core extractor 16 for extracting the blood vessel core image c using the 3-dimensional data a of the blood vessels. According to the fourth embodiment, however, the blood vessel core image c is calculated without using the 3-dimensional data a of the blood vessels.

The blood vessel core calculator 16a calculates the blood vessel core image c using two or more X-ray images d of the blood vessels taken from different X-ray photographing directions. The two or more X-ray images d of the blood vessels are obtained by the above-mentioned X-ray angiographic examination.

According to the fourth embodiment, it is possible to obtain the blood vessel core image c without using the 3-dimensional data a of the blood vessels.

[The Fifth Embodiment]

Figure 11:
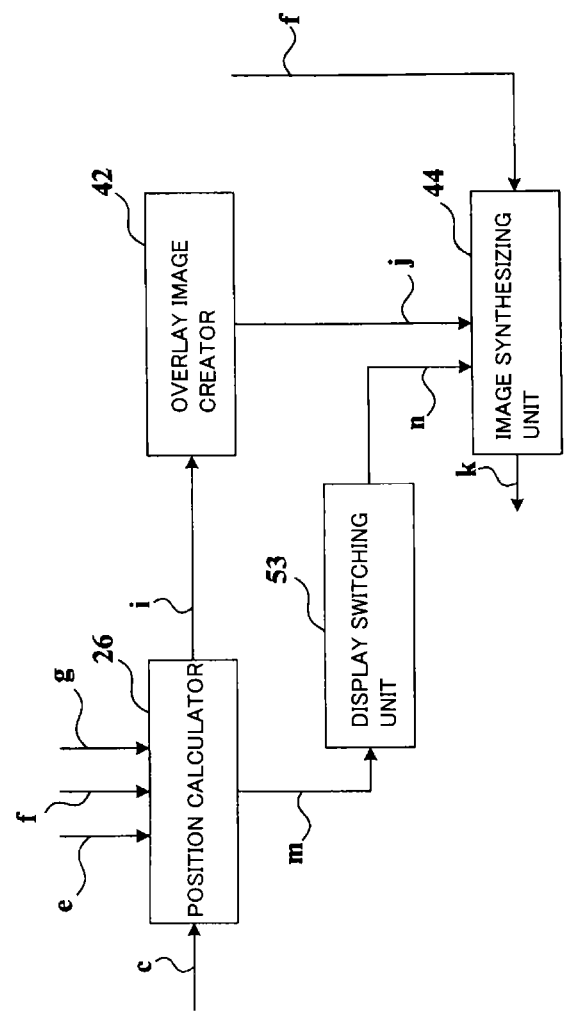
FIG. 11 is a functional block diagram according to the fifth embodiment.

Next, with reference to FIG. 11, the fifth embodiment of the image processing display device is described.

In the fifth embodiment, with respect to the elements having the same configurations as those of the first embodiment, the same numbers are provided and the explanation thereof is omitted.

In the first embodiment, it is determined whether or not the 2-dimensional image j of the distal end of the catheter is sent from the overlay image creator 12 for each predetermined time, and when the image is not sent, the image synthesizing unit 44 outputs the X-ray fluoroscopic image f to the display controller 51 as the synthesized image k.

On the contrary, according to the fifth embodiment, based on a result of determination made by the position calculator 26 regarding whether or not the catheter shadow is superimposed on the treatment apparatus image g, the image synthesizing unit 44 is instructed whether the 2-dimensional image j of the distal end of the catheter is synthesized. Further, cases in which the catheter shadow is superimposed on the treatment apparatus image f may be referred to as "cases in which the distal end of the catheter is located within the region of the X-ray fluoroscopic image showing the treatment apparatus." In addition, cases in which the catheter shadow is not superimposed on the treatment apparatus image f may be referred to as "cases in which the distal end of the catheter is located outside the region of the X-ray fluoroscopic image showing the treatment apparatus."

FIG. 11 is a functional block diagram. In FIG. 11, the result determined by the position calculator 26 is represented by "m," while a signal showing whether the 2-dimensional image j of the distal end of the catheter should be synthesized to the X-ray fluoroscopic image f is represented by "n."

As shown in FIG. 11, the fifth embodiment of the image processing display device is provided with a display switching unit 53, which outputs a signal n in order to prevent the synthesis of the image j representing the distal end position of the catheter determined by the position calculator 26 to the X-ray fluoroscopic image f upon receiving the result m from the determination made by the position calculator 26 that the distal end of the catheter is located outside the region where the treatment apparatus is present on the X-ray fluoroscopic image f. The display switching unit 53 then outputs the signal n to the image synthesizing unit 44 in order to synthesize the image j representing the distal end position of the catheter to the X-ray fluoroscopic image f upon receiving the result m from the determination that the distal end of the catheter is located within the region.

According to the fifth embodiment, the display switching unit 53 is allowed to clearly display a distal end of the catheter as a part of the X-ray fluoroscopic image f and clearly display the distal end position of the catheter as the image j, making it possible to prevent interference with the catheter treatment.

[The Sixth Embodiment]

Figure 12:
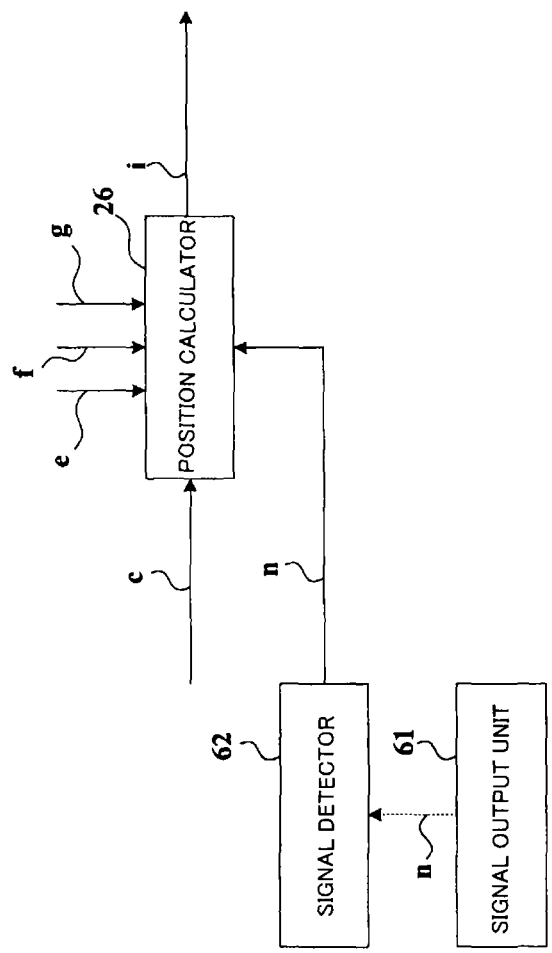
FIG. 12 is a functional block diagram according to the sixth embodiment.

Next, with reference to FIG. 12, the sixth embodiment of the image processing display device is described.

In the sixth embodiment, with respect to the elements having the same configurations as those of the first embodiment, the same numbers are provided and the explanation thereof is omitted.

In the first embodiment, using the blood vessel core image c and the operational information h according to the catheter, the position calculator 26 indirectly determines the distal end position of the catheter.

On the contrary, in the sixth embodiment, the distal end position of the catheter is directly measured.

FIG. 12 is a functional block diagram. In FIG. 12, information regarding the distal end position of the catheter is indicated by "n." This position information replaces the operational information h.

As shown in FIG. 12, the image processing display device has a signal output unit 61 and a signal detector 62.

The signal output unit 61 is, for example, a permanent magnet, and is attached to the distal end of the catheter. In FIG. 12, the intensity of the magnetic field (a magnetic signal) made by the permanent magnet is indicated by "n."

The signal detector 62, for example, is a 3-dimensional magnetic sensor, and receives the magnetic field made by the permanent magnet. As the 3-dimensional magnetic sensor, for example, a magnetic sensor board having a magnetic sensor for the 3-dimensional input, as described in Japanese Unexamined Patent Application Publication No. 8-152955, is used.

The position calculator 26 determines the 3-dimensional position information of the distal end of the catheter based on the magnetic signal "n" received by the 3-dimensional magnetic sensor.

Further, in order to increase the precision of the position when the 3-dimensional position information of the distal end of the catheter is determined, the position calculator 26 may refer to the blood vessel core image c and/or the operational information h.

In addition, the 3-dimensional position information of the distal end of the catheter is determined based on the magnetic signal; however, it is needless to say that it is not limited to the magnetic signal to determine the information.

According to the sixth embodiment, the distal end position of the catheter can be directly determined based on the magnetic signal.

Some embodiments of the present invention have been described as above; however, these embodiments are presented merely as examples and are not intended to limit the scope of the invention. These new embodiments can be carried out in other various modes and various changes including making various omissions, rewritings, and modifications can be made without departing from the scope of the invention. These embodiments and their modifications are included within the scope and subject matter of the invention, and included in the invention set forth in the scope of patent claims and an equal scope thereof.

EXPLANATION OF SYMBOLS

1 X-ray source
2 X-ray detector
13 blood stream information creator
14 storage unit
15 blood vessel core processor
16 blood vessel core extractor
16a blood vessel core calculator
22 image processor
23 positioning processor
25 image processor
26 position calculator
28 blood bifurcation determination processor
33 treatment apparatus image extractor
42 overlay image creator
44 image synthesizing unit
45 overlay determination processor
51 display controller
52 display
61 signal output unit
62 signal detector

The invention claimed is:

1. An image processing display device configured to display X-ray fluoroscopic images which are obtained by X-ray fluoroscopic imaging of blood vessels during a hybrid treatment that utilizes a treatment apparatus and a catheter, the image processing display device comprising:
 a treatment apparatus image extractor configured to extract, based on the X-ray fluoroscopic images, treatment apparatus images that represent the treatment apparatus; and
 an image processor configured to
  acquire position information of a distal end of the catheter according to
   the X-ray fluoroscopic images when the distal end of the catheter is not located in a region where the treatment apparatus is present in one of the X-ray fluoroscopic images, and
   three-dimensional blood stream information, obtained from the X-ray fluoroscopic images, and operational information related to the catheter when the distal end of the catheter is located in the region in the one of the X-ray fluoroscopic images, and
  display images corresponding to the position information of the distal end of the catheter, wherein
 when the distal end position of the catheter is located in the region where the treatment apparatus is present in the one of the X-ray fluoroscopic images, the image processor creates two-dimensional images of the distal end of the catheter according to the distal end position of the catheter, and displays the two-dimensional images superimposed in the region where the treatment apparatus is present, and
 the treatment apparatus is for bypass surgery and absorbs X-rays.

2. The image processing display device according to claim 1, wherein the image processor does not display the images corresponding to the position information of the distal end of the catheter when the distal end of the catheter is located outside the region while superimposing and displaying the images in the region when the distal end of the catheter is located within the region.

3. The image processing display device according to claim 1, comprising:
 a signal transmitter configured to output signals, the signal transmitter provided on the distal end of the catheter; and
 a signal detector configured to receive the output signals, wherein
 the image processor comprises a position calculator configured to determine the position information based on the received signals when the distal end of the catheter is determined to be not located in the region where the treatment apparatus is present in the X-ray fluoroscopic image.

4. The image processing display device according to claim 1, further comprising:
 a memory configured to store the three-dimensional blood stream information obtained prior to the hybrid treatment, wherein
 the image processor comprises a position calculator configured to determine the distal end position of the catheter based on the blood stream information and operational information according to the catheter.

5. The image processing display device according to claim 4, wherein the image processor receives X-ray images of blood vessels and, based on the positioning of the X-ray images of the blood vessels and the blood stream information, determines the corresponding positional relation between the images and the blood stream information.

6. The image processing display device according to claim 4, wherein
 the image processor comprises an overlay determination processor configured to determine an angle in the photographing direction of X-rays based on the X-ray fluoroscopic images, the angle allowing direct exposure of the distal end of the catheter without being interfered by the treatment apparatus, and
 when the two-dimensional images of the distal end of the catheter are created, the image processor further refers to the distal end position of the catheter that is determined based on the X-ray imaging data obtained by X-rays exposure at the angle in the photographing direction of X-rays.

7. The image processing display device according to claim 4, wherein
 the position calculator is configured to determine
  positions of blood bifurcations based on the blood stream information, and
  positioning information indicating a corresponding positional relation between the X-ray images of blood vessels and the blood stream information, and
 the image processor determines whether or not the positions of the blood bifurcations overlap the region where the treatment apparatus is present from information on the region where the treatment apparatus is present in the X-ray fluoroscopic image and the positions of the blood bifurcations based on the distal end position of the catheter and creates the two-dimensional images of the blood bifurcations related to the X-ray fluoroscopic images when the blood bifurcations are located behind the treatment apparatus.

8. The image processing display device according to claim 4, wherein the blood stream information includes three-dimensional blood vessel cores images representing blood vessel cores.

9. The image processing display device according to claim 8, further comprising:

a blood vessel core extractor configured to extract the blood vessel core images based on the three-dimensional blood stream information, wherein
the blood stream information is created based on the three-dimensional blood stream information of the region including the blood vessels.

10. The image processing display device according to claim 8, further comprising a blood vessel core calculator configured to calculate the blood vessel core images by analyzing blood stream information according to changes in angiograms based on X-ray images of the blood vessels created from X-ray fluoroscopic images in a plurality of time phases.

11. A non-transitory computer readable medium including computer executable instructions to execute an image processing display program during a hybrid treatment that utilizes a treatment apparatus and a catheter, which cause a computer to:
preliminarily store three-dimensional images of blood vessels, the three-dimensional images created based on three-dimensional data of a region including the blood vessels;
preliminarily obtain X-ray images of the blood vessels;
extract three-dimensional blood vessel core images, representing blood vessel cores, based on the three-dimensional data;
create X-ray fluoroscopic images based on X-ray fluoroscopic data;
extract treatment apparatus images, based on the X-ray fluoroscopic images, that represent the treatment apparatus;
determine positioning information that is a corresponding positional relation of the three-dimensional images of the blood vessels to the X-ray images of the blood vessels;
acquire position information of a distal end of the catheter according to:
the X-ray fluoroscopic images when the distal end of the catheter is not located in a region where the treatment apparatus is present in one of the X-ray fluoroscopic images, and
three-dimensional blood stream information, obtained from the X-ray fluoroscopic images, and operational information related to the catheter when the distal end of the catheter is located in the region where the treatment apparatus is present in the one of the X-ray fluoroscopic images;
display images corresponding to the position information of the distal end of the catheter; and
when the distal end position of the catheter is located in the region where the treatment apparatus is present in the one of the X-ray fluoroscopic images,
create two-dimensional images of the distal end of the catheter superimposed on the treatment apparatus images based on the distal end of the catheter and the treatment apparatus images; and
display the two-dimensional images superimposed in the region where the treatment apparatus is present, wherein
the treatment apparatus is for bypass surgery and absorbs X-rays.

* * * * *